United States Patent
Iacono

(10) Patent No.: US 8,609,155 B2
(45) Date of Patent: Dec. 17, 2013

(54) DIETARY SUPPLEMENT STIMULATING THE MALE SEXUAL FUNCTION

(75) Inventor: Fabrizio Iacono, Naples (IT)

(73) Assignee: Tradapharma SAGL, Lugano (CH)

( * ) Notice: Subject to any disclaimer, the term of this patent is extended or adjusted under 35 U.S.C. 154(b) by 0 days.

(21) Appl. No.: 13/496,360

(22) PCT Filed: Sep. 16, 2010

(86) PCT No.: PCT/EP2010/005689
§ 371 (c)(1),
(2), (4) Date: Apr. 4, 2012

(87) PCT Pub. No.: WO2011/032697
PCT Pub. Date: Mar. 24, 2011

(65) Prior Publication Data
US 2012/0189722 A1    Jul. 26, 2012

(30) Foreign Application Priority Data

Sep. 17, 2009 (IT) .............................. RM2009A0474
Feb. 19, 2010 (IT) .............................. RM2010A0068

(51) Int. Cl.
*A61K 36/00* (2006.01)
(52) U.S. Cl.
USPC ........................................................ 424/725
(58) Field of Classification Search
None
See application file for complete search history.

(56) References Cited

U.S. PATENT DOCUMENTS

| | | | |
|---|---|---|---|
| 7,015,207 B2 * | 3/2006 | Xu et al. ........................ | 514/62 |
| 8,198,320 B2 * | 6/2012 | Liang et al. ................... | 514/457 |
| 2005/0220905 A1 * | 10/2005 | Bombardelli et al. ......... | 424/739 |
| 2006/0286179 A1 * | 12/2006 | Filho et al. .................... | 424/725 |

FOREIGN PATENT DOCUMENTS

| | | |
|---|---|---|
| EP | 1652520 A2 | 5/2006 |
| KR | 2004048166 A * | 6/2004 |

OTHER PUBLICATIONS

Anonymous: "Biovis: nuovo rimedio naturale per la disfunzione erettile dell'uomo", XP002576831, Mar. 16, 2005.
Tharakan Binu et al., "Botanical Therapies in Sexual Dysfunction", XP-002576833, Phytotherapy Reseach, vol. 19, No. 6, Jun. 2005.
Anonymous: "Annie's remedy. Catuaba Erythroxylum catuabla" XP002608541, 2008.
Anonymous: "Ecklonia cava: l'alga giapponese che fa bene al cuore, alla mente e alla coppia!", XP002576832, Sep. 19, 2008.
Anonymous: "Samedical Services Srl. I nostri prodotti", XP002576829, Apr. 7, 2010.
Anonymous: "Creattivo Istant Plus 8CPS", XP002576830, Apr. 7, 2010.

* cited by examiner

*Primary Examiner* — Qiuwen Mi
(74) *Attorney, Agent, or Firm* — Lucas & Mercanti, LLP

(57) ABSTRACT

The present invention relates to dietary supplements comprising *Tribulus terrestris*, glucosamine oligosaccharide and alga *Ecklonia* comprising fat-soluble polyphenols.
The dietary supplements are useful in the prevention and/or the treatment of erectile dysfunction.

10 Claims, No Drawings

DIETARY SUPPLEMENT STIMULATING THE MALE SEXUAL FUNCTION

This application is a U.S. national stage of PCT/EP2010/005689 filed on Sep. 16, 2010 which claims priority to and the benefit of Italian Application No. RM2009A000474 filed on Sep. 17, 2009 and RM2010A000068 filed Feb. 19, 2010, the contents of which are incorporated herein by reference.

TECHNICAL FIELD OF THE INVENTION

The present invention relates to a dietary supplement useful for the prevention and/or the treatment of erectile dysfunction.

BACKGROUND OF THE INVENTION

Following the decline of the old-fashioned social taboos relating to sexuality and the introduction of molecules that effectively generate an erectile response in males, an increasing number of men consults urology and anthology specialists with a view to improving and/or curing sexual deficiencies which, until a few years ago, responded little, if at all, to conservative (non-surgical) treatments.

It is estimated that approximately 3 million men in Italy suffer from erectile dysfunction (ED) to some extent.

5-phosphodiesterase inhibitors, which improve the erectile function, have been marketed relatively recently, and have had some commercial success.

However, although these medicaments are certainly effective in improving the male erectile function in over 70% of cases, their contraindications, the sometimes serious side effects, and concern about taking chemical substances with possible multiple interactions, have greatly limited the use of these active substances, with the result that the commercial results have perhaps fallen below expectations. The enzyme 5-phosphodiesterase is present not only in the corpus cavernosum, but also in almost all the other organs, and these inhibitors, though selective, also perform an inhibitory action on other phosphodiesterases (4, 6, 11, 7, etc.) present in various known and unknown areas, the function of which is not fully understood.

Moreover, the need to take some of these substances as required (on demand), i.e. on the basis of sexual activity planned for a pre-set time, has further reduced patients' enthusiasm, leading to a very high drop-out rate from the treatment.

Moreover, in view of the high cost of the medicaments, the fact that they have low or no therapeutic effect, but only a symptomatic effect, and their total lack of efficacy on the libido, chronic treatment with 5-phosphodiesterase inhibitors and the use of molecules with a long half-life (Tadalafil) is difficult to achieve.

On the basis of experience obtained in years of studies and research into erectile dysfunction, and on the basis of knowledge of the type of andrology patients suffering from said disorder, it has been reached the conclusion that a medicament which acts on both the libido and the symptoms is required; it also needs to act constantly, without any limiting psychological side effects, and to perform also a possibly trophic action on the corpus cavernosum and improve its elasticity, which generally declines with age, leading to fibrosis (it should also be effective against Peyronie's disease or induratio penis plastica, which affects 3-6% of the male population).

However, the development of such a medicament would require years of very expensive experimentation.

There is therefore the need to find new medicaments for prevention and/or treatment of erectile dysfunction.

SUMMARY OF THE INVENTION

The present invention relates to a dietary supplement stimulating the male sexual function comprising:
 Trihulus terrestris,
 glucosamine oligosaccharide,
 alga *Ecklonia* comprising fat-soluble polyphenols.

The invention also concerns the use of the dietary supplement in the prevention and/or the treatment of erectile dysfunction.

DETAILED DESCRIPTION OF THE INVENTION

The present invention relates to a dietary supplement stimulating the male sexual function.

The supplement comprises (as active ingredients):
 *Tribulus terrestris*;
 glucosamine oligosaccharide;
 alga *Ecklonia* comprising fat-soluble polyphenols.

*Tribulas terrestris* has preferably a 40% saponin content; it naturally stimulates testosterone production, increases the libido and the trophism of the testosterone-dependent organs and improves fertility.

The glucosamine oligosaccharide is marketed for example under the trademark BIOVIS® and comprises polymers of D-glucosamine and N-acetyl-D-glucosamine. The glucosamine oligosaccharide stimulates the release of NO (nitrous oxide).

According to the invention, all the different species and sub-species of "alga *Ecklonia*" may be used in the supplement.

Alga *Ecklonia* may be selected from the group consisting of *Ecklonia bicyclis Kjellman*, *Ecklonia biruncinata* (Bory de Saint-Vincent) *Papenfuss*, *Ecklonia brevipes J. Agardh*, *Ecklonia huccinalis* (Linnaeus) *Hornemann*, *Ecklonia caepaestipes* (Montagne) *Endlicher*, *Ecklonia cava Kjellman*, *Ecklonia exasperata* (Turner) *J. Agardh*, *Ecklonia fastigiata* (Endlicher & Diesing) *Papenfuss*, *Ecklonia kurome Okamura*, *Ecklonia latifolia Kjellman*, *Ecklonia maxima* (Osbeck) *Papenfuss*, *Ecklonia muratii Feldmann*, *Ecklonia radiata* (C. Agardh) *J. Agardh*, *Ecklonia radiata* var. *exasperata* (Turner) *Harvey*, *Ecklonia radiata f. exasperata* (Turner) *De Toni*, *Ecklonia radiata f. biruncinata* (Bory de Saint-Vincent) *Papenfuss*, *Ecklonia radicosa* (Kjellman) *Okamura*, *Ecklonia richardiana J. Agardh*, *Ecklonia stolonifera Okamura*, *Ecklonia wrightii Harvey*.

In a preferred embodiment, alga *Ecklonia*, which comprises fat-soluble polyphenols, is selected from alga *Ecklonia Cava*, alga *Ecklonia Bicyclis* (also known as *Eisenia Bicyclis*).

Alga *Ecklonia Cava* is marketed for example under the trademark SEANOL®.

The fat-soluble polyphenols improves the erectile function.

Preferably, the ingredients present in the supplement, according to the invention, are:
 *Tribulas terrestris*, with a 40% saponin content,
 glucosamine oligosaccharide,
 alga *Ecklonia Cava* or *Bicyclis*.

The ingredients of the dietary supplement may vary as follows:
 *Tribulas terrestris*: from 200 mg to 500 mg per dosage unit;
 alga *Ecklonia* comprising fat-soluble polyphenols: from 50 mg to 600 mg per dosage unit;

glucosamine oligosaccharide: from 100 mg to 150 mg per dosage unit.

Experiments have demonstrated that a supplement comprising the following active ingredients:

Tribulus Terrestris, with a 40% saponin content, at the dose of 200 mg per dosage unit;
glucosamine oligosaccharide, at the dose of 100 mg per dosage unit; and
alga Ecklonia Cava or Bicyclis, at the dose of 250 mg per dosage unit of dried Ecklonia extract,
gives satisfactory results after only one treatment cycle.

The experiments conducted showed that by proportionally increasing the quantities of ingredients in each dosage unit, the number of dosage units which the patient needs to take to obtain the same result can be reduced.

A reduction in the number of dosage units to be taken by the patient can be obtained, for example, with the following quantities of ingredients:

Tribulus terrestris, with a 40% saponin content, at the dose of 500 mg per dosage unit;
glucosamine oligosaccharide, at the dose of 150 mg per dosage unit;
alga Ecklonia cava or Bicyclis, at the dose of 600 mg per dosage unit of dried Ecklonia extract; or
Tribulus terrestris, with a 40% saponin content, at the dose of 350 mg per dosage unit;
glucosamine oligosaccharide, at the dose of 150 mg per dosage unit;
alga Ecklonia Cava or Bicyclis, at the dose of 400 mg per dosage unit of dried Ecklonia extract.

According to another embodiment, the supplement further comprises Cnidium Monnieri.

Cnidium Monnieri has a muscle-relaxant effect on the corpora cavernosa by releasing NO.

Cnidium Monnieri is usually added at a dose ranging between 50 mg and 300 mg per dosage unit.

The following supplement may be obtained with the addition of Cnidium Monnieri:

Tribulus terrestris: from 200 mg to 500 mg per dosage unit;
alga Ecklonia comprising fat-soluble polyphenols: from 50 mg to 600 mg per dosage unit;
glucosamine oligosaccharide: from 100 mg to 150 mg per dosage unit;
Cnidium Monnieri: from 50 mg to 300 mg per dosage unit.

According to another embodiment, the supplement further comprises Anentopaegma Mirandum Mart. ex DC (Catuaba), in particular Catuaba bark.

Catuaba is usually added at a dose ranging between 50 mg and 300 mg per dosage unit.

The following supplement may be obtained with the addition of Catuaba:

Tribulus terrestris: from 200 mg to 500 mg per dosage unit;
alga Ecklonia comprising fat-soluble polyphenols: from 50 mg to 600 mg per dosage unit;
glucosamine oligosaccharide: from 100 mg to 150 mg per dosage unit;
Catuaba: from 50 mg to 300 mg per dosage unit.

The dietary supplements may be formulated by conventional methods. Preferred dosage forms are capsules, sachets.

The dietary supplement according to the invention does not present the drawbacks of the medicaments currently on the market, and in particular has the following advantages, compared to the conventional medicaments:

greater compliance of patients to take a natural product/extract;
lower cost;
curative and symptomatic action;
no significant side effects;
no pharmacological contraindications;
effect on libido;
possible effect on fertility, thereby extending the range of indications (many men undergoing fertility treatment complain of loss of libido and erectile difficulties, nearly always due to psychological problems);
no delayed ejaculation;
3-month treatment cycles;
no need to take the product before sexual intercourse;
curative properties and improved erectile functions;
prevention of senile fibrotic degeneration of the corpora cavernosa, which means that it can also be used by healthy men;
no psychological implications for the patient, because the erectile dysfunction is not treated with a medicine, and is consequently not perceived as an illness by the patient or his partner.

The supplement according to the invention includes substances which improve both the libido and the erectile function.

EXAMPLES

Example 1

Dietary Supplement

Supplement a)
The supplement comprises:
Tribulus terrestris, with a 40% saponin content: 400 mg per dosage unit;
alga Ecklonia Cava dry extract: 150 mg per dosage unit;
glucosamine oligosaccharide: 144 mg per dosage unit.

Supplement b)
The supplement comprises:
Tribulus terrestris, with a 40% saponin content: 400 mg per dosage unit;
alga Ecklonia Bicyclis dry extract: 150 mg per dosage unit;
glucosamine oligosaccharide: 144 mg per dosage unit.

Example 2

Biological Data

The therapeutical efficacy of a dietary supplement comprising Tribulus terrestris, glucosamine oligosaccharide and alga. Ecklonia (comprising fat-soluble polyphenols) in the treatment of male sexual dysfunction has been investigated.

Patients have been selected on the basis of the International Index of Erectile Function, the Nocturnal Penile Tumescence, the Rigidometry Test (NPTR) with RigiScan® device and the hormonal levels.

82 patients (pts) with erectile dysfunction (ED), without previous treatment for the ED were enrolled for study inclusion. The mean age of the pts was 53.1 years.

Patients with concomitant diseases were included in the study, if they had stable disease with concurrent medical therapy for cardiovascular disease, diabetes and so forth.

All the patients at baseline were evaluated with medical and psychosexual history to detect co-morbidities. Organic co-morbidities included hypertension in 23 pts (28.1%), diabetes in 12 pts (14.6%) and abnormal total serum cholesterol in 7 pts (8.5%).

IIEF questionnaire (pre and post treatment) was carried out on all the pts and also Nocturnal Penile Tumescence and Rigidometry Test (NPTR) by RigiScan® device (pre and post treatment) was performed.

The IIEF questionnaire was administered to each patient and the serum level of baseline testosterone was checked.

All the patients, after HU questionnaire, were divided into three groups: 1) group A, 32 pts (36.6%) affected by mild ED (IIEF score over 16);

2) group B, 31 pts (35.4%) affected by moderate ED (IIEF score between 11 and 16);

3) group C, 19 pts (19.5%) affected by severe ED (IIEF score below 10).

For each group has been reported (Table 1): erectile function (AREA 1), orgasmic function (AREA 2), sexual desire (AREA 3), intercourse satisfaction (AREA 4), overall satisfaction (AREA 5).

Moreover, all the patients were examined by penile dynamic Doppler ultrasonography and tested with NPRT using the RigiScan® device (UroHealth Systems, Laguna Niguel, Calif.), to determine related baseline parameters, including rigidity, number and lasting of the nocturnal penile erections.

After baseline evaluation, all the patients were treated for 8 weeks with the dietary supplement (150 mg of alga *Ecklonia*, 400 mg of *Tribulus terrestris* and 144 mg of glucosamine oligosaccharide) administered to all the pts twice a day.

IIEF was administered, testosterone level was valued and NPTR was measured after the period of treatment.

The Mann-Whitney test has been used to determine the statistical significance of responses to global efficacy question, with the paired Student t test with significance considered at $p<0.01$.

At the end of the treatment 75 patients were evaluable.

In Table 1 the improvement in the IIEF after the 60 days of treatment in the three groups of the 75 evaluable patients is reported.

The IIEF scores were significantly improved in all the pts with an increase of 78% in mild ED group, while in the moderate ED group there was an improvement of 80% and in the severe ED group of 108% from the baseline.

Group A showed an improvement in all domains of IIEF questionnaire scores, with a significant improvement after 8 weeks of treatment (from baseline 22.1+/−1.6 to 39.3+/−5.1 p<0.01).

Also Group B showed an improvement in all domains of IIEF questionnaire, with a significant improvement after 8 weeks of treatment (from baseline 14.1+/−1.5 to 25.4+/−1.8 p<0.01).

The third group (C) showed an improvement in all domains of IIEF questionnaire. Mean IIEF scores showed significant improvement after 8 weeks of treatment (from baseline 6.7+/−1.4 to 13.9+/−2.0 p<0.01).

Table 1 shows IIEF scores in three groups (A, B, C) before and after the treatment.

TABLE 1

|  |  | IIEF (total score) | AREA 1 | AREA 2 | AREA 3 | AREA 4 | AREA 5 |
|---|---|---|---|---|---|---|---|
| GROUP A | pre-treatment | 22.1 +/− 1.6 | 5.8 +/− 0.4 | 5.3 +/− 1.5 | 4.1 +/− 1.7 | 4.3 +/− 1.0 | 2.5 +/− 0.8 |
|  | post-treatment | 39.3 +/− 5.1 (p < 0.01) | 11.2 +/− 2.0 (p < 0.01) | 5.9 +/− 1.6 (no significant difference) | 8.7 +/− 1.2 (p < 0.01) | 7.1 +/− 1.9 (p < 0.01) | 6.3 +/− 1.5 (p < 0.01) |
| GROUP B | pre-treatment | 14.1 +/− 1.5 | 4.7 +/− 1.2 | 2.4 +/− 0.8 | 3.0 +/− 0.9 | 1.8 +/− 0.4 | 2.2 +/− 0.4 |
|  | post-treatment | 25.4 +/− 1.8 (p < 0.01) | 8.4 +/− 1.6 (p < 0.01) | 2.9 +/− 1.0 (no significant difference) | 7.5 +/− (p < 0.01) | 3.1 +/− 0.9 (p < 0.01) | 3.6 +/− 0.7 (p < 0.01) |
| GROUP C | pre-treatment | 6.7 +/− 1.4 | 1.8 +/− 0.9 | 0.0 +/− 0.0 | 2.3 +/− 0.7 | 0.6 +/− 1.7 | 2.1 +/− 0.3 |
|  | post-treatment | 13.9 +/− 2.0 (p < 0.01) | 3.3 +/− 1.1 (p < 0.01) | 0.5 +/− 0.9 (no significant difference) | 6.0 +/− 1.7 (p < 0.01) | 1.6 +/− 1.0 (no significant difference) | 2.6 +/− 0.6 (p < 0.01) |

In table 2 mean baseline values of the three RigiScan® items (nocturnal erection number, percentage of penile rigidity and lasting of the nocturnal erections) and the changes in RigiScan® data before and after the treatment in the 75 evaluable patients are reported.

It has been noted that the mean RigiScan® parameters revealed, in all three groups, significative increase in terms of number of nocturnal erections and percentile scale tumescence of the penis. In fact RigiScan® is improved in the 93.7% of the population.

It has been found, in particular, in Group A: a 17% increase of the number of spontaneous erections and a 11% increase of the mean percentage of rigidity; in Group B; 39% and 6% respectively and 75% and 38% respectively in the Group C.

TABLE 2

|  |  | NUMBER OF ERECTION (N°) | RIGIDITY (%) | DURATION (min) |
|---|---|---|---|---|
| GROUP A | pre-treatment | 3.5 +/− 0.9 | 70.5 +/− 4.2% | 13.7 +/− 1.4 |
|  | post-treatment | 4.1 +/− 0.7 (p < 0.01) | 78.1 +/− 5.0% (p < 0.01) | 14.0 +/− 1.6 |
| GROUP B | pre-treatment | 1.8 +/− 0.7 | 62.6 +/− 3.6% | 9.6 +/− 1.4 |
|  | post-treatment | 2.5 +/− 0.5 (p < 0.01) | 66.6 +/− 2.8% (p < 0.01) | 10.0 +/− 1.3 |
| GROUP C | pre-treatment | 0.8 +/− 0.4 | 44.3 +/− 20.8% | 5.2 +/− 3.0 |
|  | post-treatment | 1.4 +/− 0.5 (p < 0.01) | 61.2 +/− 2.9% (p < 0.01) | 6.3 +/− 2.2 |

In table 3 patient's mean baseline, in the group A, of serum level of testosterone was 5.3+/−1.1 ng/ml (normal range: 2.8 to 9.8 ng/ml).

In the group B testosterone serum level was 5.0+/−1.1 ng/ml; and in the group C was 5.0+/1.0 ng/ml.

Table 3 shows the changes in mean testosterone serum: an increase of 28% in the Group A, 20% in the Group B and 24% in the Group C has been noted.

Despite the increase of the testosteronemia in the 93.7% of the population, there was not a contextual significant increase of the PSA.

These results indicate a specific efficacy of the dietary supplement in the treatment of erectile dysfunction.

TABLE 3

|  |  | Testosterone (ng/ml) |
|---|---|---|
| GROUP A | pre-treatment | 5.3 +/− 1.1 |
|  | post-treatment | 6.8 +/− 1.6 |
|  |  | (p < 0.01) |
| GROUP B | pre-treatment | 5.0 +/− 1.1 |
|  | post-treatment | 6.0 +/− 1.2 |
|  |  | (p < 0.01) |
| GROUP C | pre-treatment | 5.0 +/− 1.0 |
|  | post-treatment | 6.2 +/− 1.3 |
|  |  | (p < 0.01) |

As reported in table 4, patient's mean baseline of serum level of total PSA was 1.8+/−0.6 (normal range: 0 to 4 ng/ml) in group A, 1.9+/−0.2 in group B and 1.8+/−0.1 in Group C.

Moreover, there was no statistically significant difference regarding PSA in treated patients (Table 4).

TABLE 4

|  | PSA (ng/ml) |
|---|---|
| GROUP A |  |
| pre-treatment | 1.8 +/− 0.6 |
| post-treatment | 1.8 +/− 0.3 |
| GROUP B |  |
| pre-treatment | 1.9 +/− 0.2 |
| post-treatment | 1.9 +/− 0.5 |
| GROUP C |  |
| pre-treatment | 1.8 +/− 0.1 |
| post-treatment | 1.7 +/− 0.9 |

The combination of the active ingredients seems to work in synergy, not just improving the erectile function but stimulating the T dependent sexual desire too.

The study demonstrated that the dietary supplement was effective in the oral treatment of ED.

The invention claimed is:

1. A dietary supplement stimulating the male sexual function comprising:
   *Tribulus terrestris*,
   glucosamine oligosaccharide,
   alga *Ecklonia* comprising fat-soluble polyphenols.

2. The dietary supplement according to claim 1, wherein the alga *Ecklonia* is *Ecknonia cava* or *Ecklonia bicyclis*.

3. The dietary supplement according to claim 1, comprising:
   *Tribulus terrestris*, with a 40% saponin content,
   glucosamine oligosaccharide, and alga *Ecknonia cava* or *Ecklonia bicyclis*.

4. The dietary supplement according to claim 1, wherein the ingredients vary in the following dosage ranges:
   *Tribulus terrestris* from 200 mg to 500 mg per dosage unit,
   alga *Ecklonia* comprising fat-soluble polyphenols from 50 mg to 600 mg per dosage unit,
   glucosamine oligosaccharide from 100 mg to 150 mg per dosage unit.

5. The dietary supplement according to claim 1, further comprising *Cnidium Monnieri*.

6. The dietary supplement according to claim 5, wherein *Cnidium Monnieri* ranges from 50 mg to 300 mg per dosage unit.

7. The dietary supplement according to claim 1, further comprising *Catuaba*.

8. The dietary supplement according to claim 7, wherein *Catuaba* ranges from 50 mg to 300 mg per dosage unit.

9. The dietary supplement according to claim 1, in the form of capsule or sachet.

10. The dietary supplement according to claim 1, for use in reducing the incidence of or treating erectile dysfunction.

* * * * *